(12) United States Patent
Maris

(10) Patent No.: US 6,317,216 B1
(45) Date of Patent: Nov. 13, 2001

(54) OPTICAL METHOD FOR THE DETERMINATION OF GRAIN ORIENTATION IN FILMS

(75) Inventor: Humphrey J. Maris, Barrington, RI (US)

(73) Assignee: Brown University Research Foundation, Providence, RI (US)

( * ) Notice: Subject to any disclaimer, the term of this patent is extended or adjusted under 35 U.S.C. 154(b) by 0 days.

(21) Appl. No.: 09/459,701

(22) Filed: Dec. 13, 1999

(51) Int. Cl.⁷ .................................................. G01B 9/02

(52) U.S. Cl. ...................... 356/496; 356/432 T; 356/502; 356/503

(58) Field of Search ................................ 356/496, 432 T, 356/502, 503, 511

(56) References Cited

U.S. PATENT DOCUMENTS

| | | | |
|---|---|---|---|
| 3,950,987 | 4/1976 | Slezinger et al. | 73/141 A |
| 4,484,820 | 11/1984 | Rosencwaig | 374/6 |
| 4,522,510 | 6/1985 | Rosencwaig et al. | 374/7 |
| 4,579,463 | 4/1986 | Rosencwaig et al. | 374/57 |
| 4,632,561 | 12/1986 | Rosencwaig et al. | 356/432 |
| 4,636,088 | 1/1987 | Rosencwaig et al. | 374/5 |
| 4,679,946 | 7/1987 | Rosencwaig et al. | 374/5 |
| 4,710,030 | 12/1987 | Tauc et al. | 356/32 |
| 4,710,060 | 12/1987 | Tauc et al. | 356/432 |
| 4,750,822 | 6/1988 | Rosencwaig et al. | 356/445 |
| 4,795,260 | 1/1989 | Schuur et al. | 356/400 |
| 4,844,617 | 7/1989 | Kelderman | 356/372 |
| 4,854,710 | 8/1989 | Opsal et al. | 356/432 |

(List continued on next page.)

OTHER PUBLICATIONS

W. Lee Smith et al. "Ion implant monitoring with thermal wave technology". Appl. Phys. Lett . . . vol. 47. No. 6, Sep. 15, 1985, p. 584–586.

J. Opsal et al. "Thermal and plasma wave depth profiling in silicon". Appl. Phys. Lett. vol. 47, No. 5, Sep. 1, 1985, p. 498–500.

A. Rosencwaig et al. "Thin–film thickness measurements with thermal waves". Appl. Phys. Lett., vol. 43, No. 2, Jul. 15, 1983, p. 166–168.

A. Rosencwaig et al. "Detection of thermal waves through optical reflectance". Appl. Phys. Lett., vol. 46 No. 11, Jun. 1, 1985, p. 1013–1015.

A. Elci et al. "Physics of Ultrafast Phenomena in Solid State Plasmas". Solid–State Electronics, vol. 21, 1978, p. 151–158.

(List continued on next page.)

Primary Examiner—Frank G. Font
Assistant Examiner—Andrew H. Lee
(74) Attorney, Agent, or Firm—Harrington & Smith LLP

(57) ABSTRACT

A method for the determination of grain orientation in a film sample is provided comprising the steps of measuring a first transient optical response of the film and determining the contribution to the transient optical response arising from a change in the energy distribution of the electrons in the sample, determining the contribution to the transient optical response arising from a propagating strain pulse within the sample, and determining the contribution to the transient optical response arising from a change in sample temperature of the sample. The grain orientation of the sample may be determined using the contributions to the transient optical response arising from the change in the energy distribution of the electrons, the propagating strain pulse, and the change in sample temperature. Additionally, a method for determination of the thickness of a film sample is provided. The grain orientation of the sample is first determined. The grain orientation, together with the velocity of sound and a propagation time of a strain pulse through the sample are then used to determine the thickness of the film sample.

18 Claims, 11 Drawing Sheets

U.S. PATENT DOCUMENTS

| | | | |
|---|---|---|---|
| 4,952,063 | 8/1990 | Opsal et al. | 356/432 |
| 4,999,014 | 3/1991 | Gold et al. | 356/382 |
| 5,042,951 | 8/1991 | Gold et al. | 356/369 |
| 5,042,952 | 8/1991 | Opsal et al. | 356/432 |
| 5,074,669 | 12/1991 | Opsal | 356/445 |
| 5,083,869 | 1/1992 | Nakata et al. | 356/432 |
| 5,227,912 | 7/1993 | Ho et al. | 359/578 |
| 5,379,109 | 1/1995 | Gaskill et al. | 356/445 |
| 5,481,475 | 1/1996 | Young | 364/578 |
| 5,546,811 | 8/1996 | Rogers et al. | 73/800 |
| 5,574,562 | 11/1996 | Fishman et al. | 356/432 |
| 5,585,921 | 12/1996 | Pepper et al. | 356/357 |
| 5,706,094 * | 1/1998 | Maris | 356/432 |
| 5,748,317 * | 5/1998 | Maris et al. | 356/432 |
| 5,748,318 * | 5/1998 | Maris et al. | 356/361 |
| 5,844,684 * | 12/1998 | Maris et al. | 356/432 |
| 5,959,735 * | 9/1999 | Maris et al. | 356/381 |
| 6,008,906 * | 12/1999 | Maris | 356/432 |
| 6,025,918 * | 2/2000 | Maris | 356/388 |
| 6,038,026 * | 3/2000 | Maris | 356/357 |
| 6,175,416 * | 1/2001 | Maris et al. | 356/381 |
| 6,191,855 * | 2/2001 | Maris | 356/357 |
| 6,208,418 * | 3/2001 | Maris | 356/388 |
| 6,208,421 * | 3/2001 | Maris et al. | 356/432 |
| 6,211,961 * | 3/2000 | Maris | 356/432 |

OTHER PUBLICATIONS

D.H. Auston et al. "Picosecond Spectroscopy of Semiconductors". Solid–State Electronics, vol. 21, 1978, p. 147–150.

D. A. Young et al., "Heat Flow in Glasses on a Picosecond Timescale", Dept. of Engineering, Brown University, Providence, RI 1986, p. 49–51.

D. H. Auston et al. "Picosecond Ellipsometry of Transient Electron–Hole Plasmas in Germanium". Physical Review Letters, vol. 32 No. 20. May 20, 1974, p. 1120–1123.

R.J. Stoner et al. "Kapitza conductance and heat flow between solids at temperatures from 50 to 300K". Physical Review B, vol. 48, No. 22, Dec. 1, 1993 p. 16 373– 16 387.

R.J. Stoner et al. "Measurements of the Kapitza Conductance between Diamond and Several Metals". Physical Review Letters, vol. 68 No. 10, Mar. 9, 1992 p. 1563–1566.

S. Sumie et al. "A New Method of Photothermal Displacement Measurement by Laser Interferometric Probe". Jpn. J. Appl. Phys. vol. 31 Pt. 1, No. 11, 1992 p. 3575–3583.

S. Sumie et al. J.Appl. Phys. 76(10), Nov. 15, 1994 p. 5681–5689.

* cited by examiner

OPTICAL METHOD FOR THE DETERMINATION OF GRAIN ORIENTATION IN FILMS

CROSS-REFERENCE TO A RELATED PATENT APPLICATION

This patent application is related to U.S. Pat. No. 6,038,026 filed Jul. 7, 1998, entitled "Apparatus and Method for the Determination of Grain Size in Thin Films." The disclosure of this related application is incorporated by reference in its entirety insofar as it does not conflict with the teachings of the present invention.

STATEMENT OF GOVERNMENT RIGHTS

This invention was made with government support under Grant No. DE-FG02-86ER45267 awarded by the Department of Energy. The Government has certain rights in this invention

FIELD OF THE INVENTION

This invention relates generally to a method for characterizing a sample composed of one or more thin films through the use of short pulses of electromagnetic radiation. A light pulse is absorbed at the surface of the sample. The absorption of the light pulse results in a time-dependent change $\Delta R(t)$ in the optical reflectivity of the sample, and this change is measured by means of a time-delayed probe beam pulse. Analysis of the measured $\Delta R(t)$ is used to deduce the crystallographic orientation of the grains in the sample.

BACKGROUND OF THE INVENTION

Currently, in the semiconductor industry there is a great interest in the characterization of thin films. Integrated circuits are made up of a large number of thin films deposited onto a semiconductor substrate, such as silicon. The thin films include metals to make connections between the transistors making up the chip, and insulating films to provide insulation between the metal layers (see: S. A. Campbell, The Science and Engineering of Microelectronic Fabrication, Oxford University Press, (1996)). The metal films (interconnects) are typically arranged as a series of patterned layers. At the present time there may be 4 or 5 layers of interconnects. It is likely that as more complex integrated circuits are developed which will require a greater number of interconnections, the number of layers will increase. Metals of current interest include, for example, aluminum, cobalt, copper, titanium, and silicides. Insulating films include, for example, oxide glasses of various compositions and polymers.

In the production of integrated circuits it is essential that all aspects of the process be controlled as closely as possible. For metal films, it is desirable to measure properties such as the film thickness, the electrical resistivity, the grain size, the grain orientation, and the roughness of the surfaces of the film.

Currently available techniques for the determination of grain orientation include the following.
1) Electron Back-Scatter Diffraction. A sharply-focussed electron beam is directed onto the surface of the sample at an oblique angle. The back-scattered electrons diffracted from the atomic planes within the sample are detected. The intensity of these electrons form characteristic patterns, referred to as Kikuchi lines. From the angular positions of these lines, the crystallographic orientation of the atoms in the region of the sample 10 where the electron beam is incident can be determined. It is possible to scan the electron beam across the sample, and to determine how the crystallographic orientation varies from grain to grain. In this way the distribution of grain orientations can be obtained. This method has the disadvantage that a considerable amount of time is required to make a measurement. In addition, the sample 10 has to be placed into a high-vacuum chamber for the measurement to be made.
2) Transmission electron microscopy. In this technique the diffraction of high energy electrons passing through the sample is measured. The grain orientation can be determined from the diffraction pattern. To make this type of measurement, it is essential to reduce the thickness of the sample so that high energy electrons can be transmitted. Thus, the method suffers from the disadvantage that the sample is destroyed. A second disadvantage is that the preparation of the sample takes a considerable amount of time. A third disadvantage is that the sample has to be placed into a high-vacuum chamber for the measurement to be made.
3) X-Ray Diffraction: In this technique X-rays are directed onto the surface of the film, and the diffracted X-rays are detected to determine the grain orientation. This method cannot be used for rapid measurements of grain orientation.

OBJECTS OF THE INVENTION

It is a first object of this invention to provide a method for the rapid determination of the grain orientation in a metal film.

It is a further object of this invention to determine the grain orientation without making contact to the film or causing the destruction of the film.

It is a further object of this invention to determine the orientation of the grains in a sample, to calculate the sound velocity for this orientation, and then to use this sound velocity together with a measurement of the time for a strain pulse to propagate through the sample in order to determine the film thickness.

SUMMARY OF THE INVENTION

In accordance with a first embodiment of the present invention, a non-destructive system for characterizing a thin film is provided, including a non-destructive system and method for measuring at least one transient response of a structure to a pump pulse of optical radiation, the measured transient response or responses including at least one of a measurement of a modulated change $\Delta R$ in an intensity of a reflected portion of a probe pulse, a change $\Delta P$ in a polarization of the reflected probe pulse, a change $\Delta_\phi$ in an optical phase of the reflected probe pulse, and a change in an angle of reflection $\Delta_\beta$ of the probe pulse, each of which may be considered as a change in a characteristic of a reflected or transmitted portion of the probe pulse. The measured transient response or responses are then associated with at least one characteristic of interest of the structure.

The non-destructive system comprises a stage, an optical system for applying an optical pump pulse and an optical probe pulse to the film, a detector for detecting a change in optical response with respect to time, and a mechanism for changing strain in the thin film. The stage holds a substrate of a predetermined thickness and the film is located on a first side of the substrate. The optical system applies the pump pulse and the probe pulse to a free surface of the thin film such that the probe pulse is temporally delayed from the pump pulse. The detector detects the change in optical response with respect to time of the probe pulse reflected from the surface of the thin film. The mechanism for changing the strain in the thin film changes the strain from an initial strain value to a different strain value.

In accordance with a first aspect of the present invention, a method for the determination of grain orientation in a film sample is provided. The method includes the steps of measuring a first change in optical response of the film, and analyzing this change into components arising from 1) the change in the electron distribution that occurs shortly after the application of the pump pulse, 2) the propagation of strain pulses in the film, and 3) the change in temperature in the film. From these components of the change in optical response, the grain orientation in the sample is determined.

In accordance with a second aspect of the present invention, a method for the determination of the thickness of a film sample is provided. The grain orientation of the sample is first determined. The grain orientation, together with the velocity of sound and a propagation time of a strain pulse through the sample, are then used to determine the thickness of the film sample.

BRIEF DESCRIPTION OF THE DRAWINGS

The above set forth and other features of the invention are made more apparent in the ensuing Detailed Description of the Invention when read in conjunction with the attached Drawings, wherein:

FIG. 1A' illustrates a portion of FIG. 1A in greater detail;

DETAILED DESCRIPTION OF THE INVENTION

The teaching of this invention is practiced with an optical generator and a detector of a stress wave within a sample. The sample is comprised of a substrate having at least one metal film deposited thereon. The metal film may be made of aluminum, cobalt, copper, or titanium, titanium nitride, polysilicon, or any other suitable metal. The thickness of the film could range from, for example, 100A to 10 $\mu$. In this system, a non-destructive first light pulse is directed onto the sample. This first light pulse, referred to hereafter as a pump beam, is absorbed in a thin layer at the top surface of the sample. The absorption of the pump pulse results in a change $\Delta R(t)$ in the optical reflectivity of the metal film that is measured by means of a second light pulse directed at the sample. This second light pulse, referred to hereafter as a probe beam, is time-delayed relative to the pump beam. Physical properties of the film are measured by observing the transient optical response (e.g. changes in the reflected probe beam intensity).

When the pump beam is absorbed, the electrons near the surface of the metal film are excited to higher energy states, the temperature of the surface layer is increased, and the material in the surface layer tries to expand. This launches a strain pulse which propagates into the film. When this strain pulse reaches the film-substrate interface, a part of the strain pulse is reflected back towards the top surface of the film. When the strain pulse reaches the top surface of the film, the change in strain associated with the propagating pulse results in a change in the optical constants of the metal. This change leads to a sudden change $\Delta R_{strain}(t)$ in the optical reflectivity R of the metal film. The optical reflectivity R, also changes by an amount $\Delta R_{electron}(t)$ due to the excitation of the electrons to higher energy states and by an amount $\Delta R_{thermal}$ due to the change in temperature in the film. Thus, the total change in reflectivity $\Delta R(t)$ that is measured is $\Delta R_{electron}(t)+\Delta R_{strain}(t)+\Delta R_{thermal}$.

To determine the grain orientation of the sample, the change $\Delta R(t)$ is measured, divided into the three components just described, and these components are analyzed.

Figure 1A:
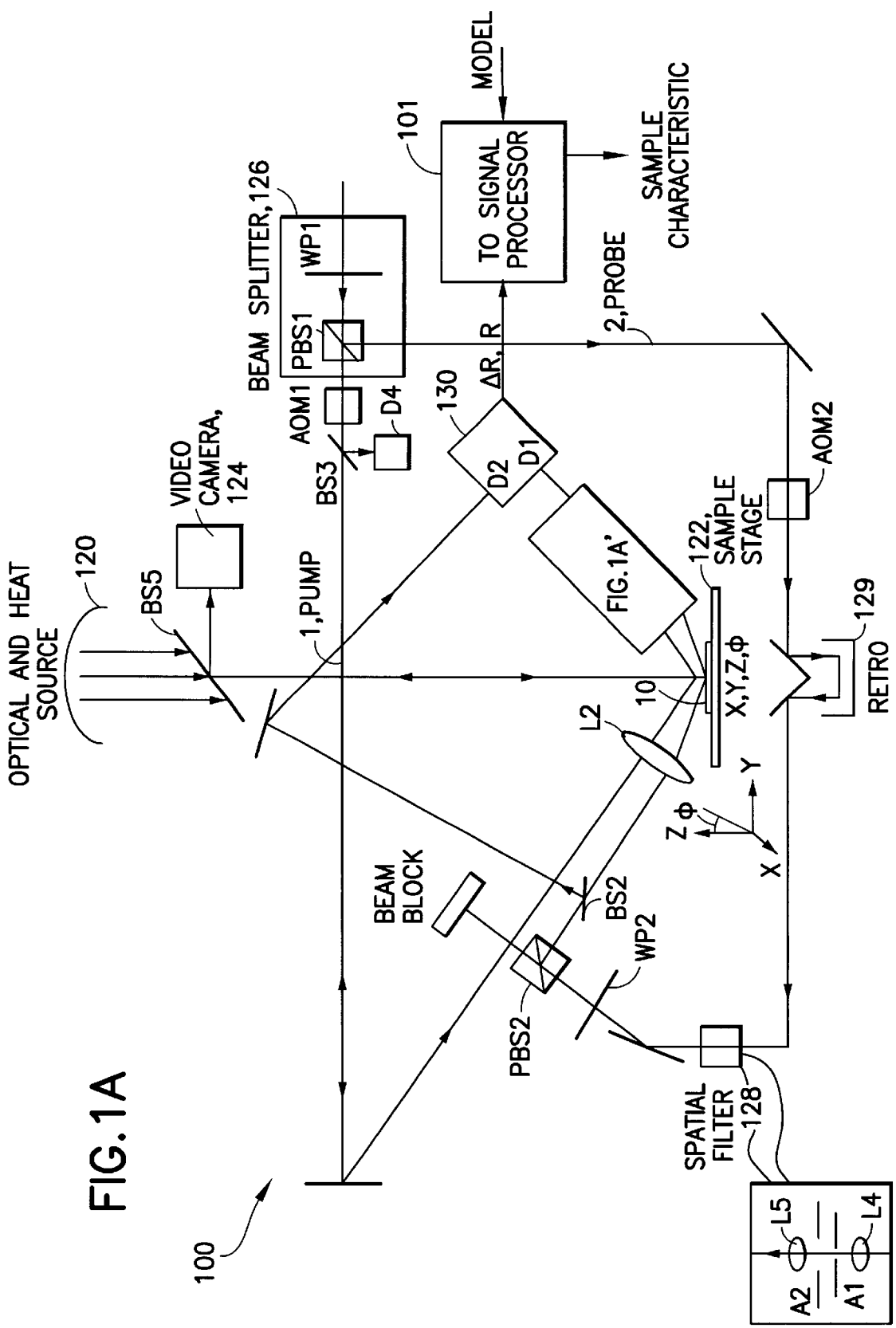
FIG. 1A is a block diagram of a first embodiment of an ultra-fast optical system that is suitable for use in practicing this invention, specifically, a parallel, oblique beam embodiment.
Figure 1A:
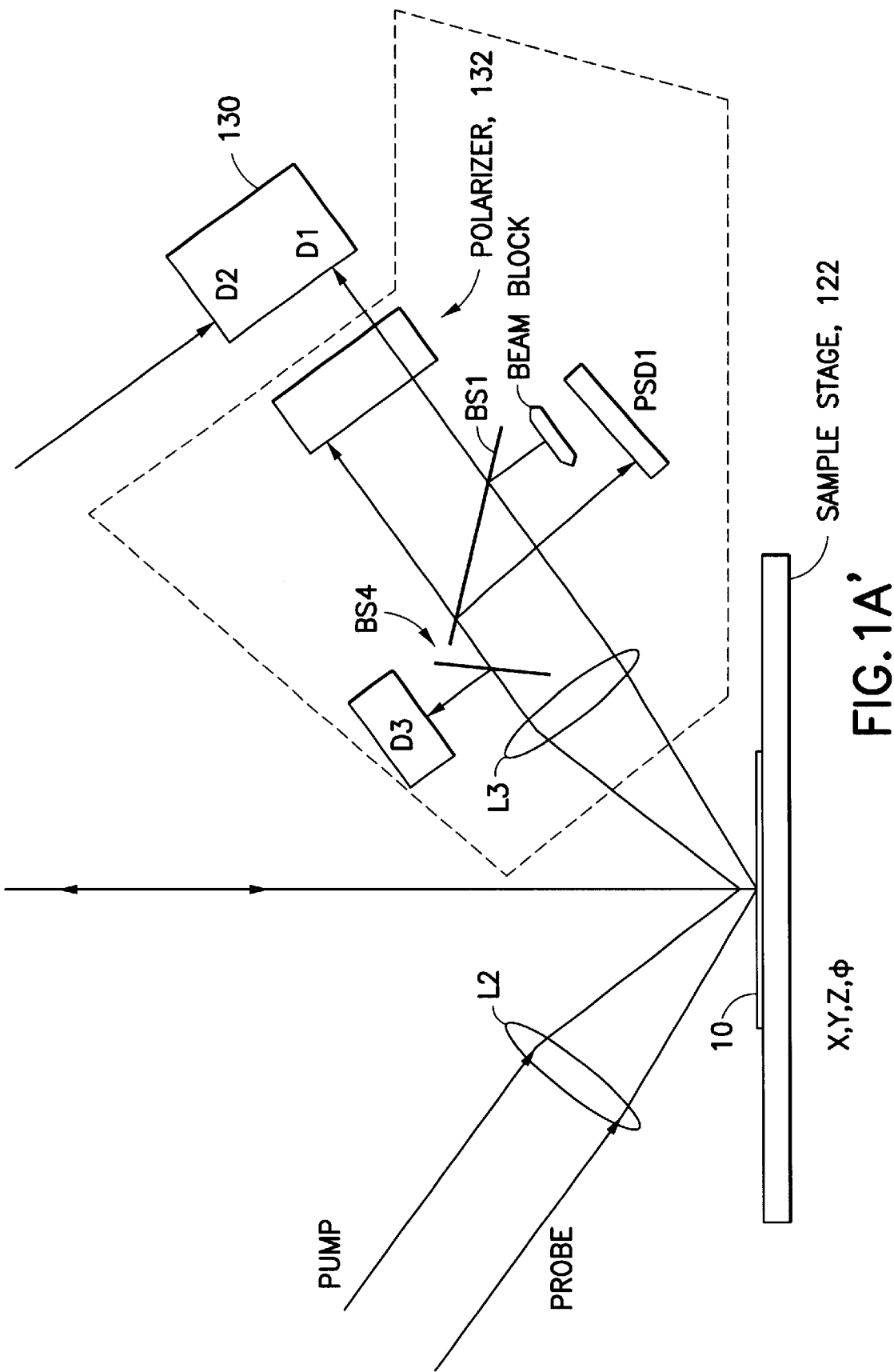

Reference is now made to FIG. 1A and FIG. 1A', collectively referred to below as FIG. 1A, for illustrating a first embodiment of an apparatus 100 suitable for practicing this invention. This embodiment is referred to as a parallel, oblique embodiment.

This embodiment includes an optical/heat source 120, which functions as a variable high density illuminator, and which provides illumination for a video camera 124 and a sample heat source for temperature-dependent measurements under computer control. An alternative heating method employs a resistive heater embedded in a sample stage 122. One advantage of the optical heater is that it makes possible rapid sequential measurements at different temperatures, or at one stabilized temperature.

The video camera 124 provides a displayed image for an operator, and facilitates the set-up of the measurement system. Appropriate pattern recognition software can also be used for this purpose, thereby minimizing or eliminating operator involvement. BS5 is a broad band beam splitter that directs video and a small amount of laser light to the video camera 124. The camera 124 and processor 101 can be used to automatically position the pump beam 1 and the probe beam 2 on a measurement site.

Figure 4:
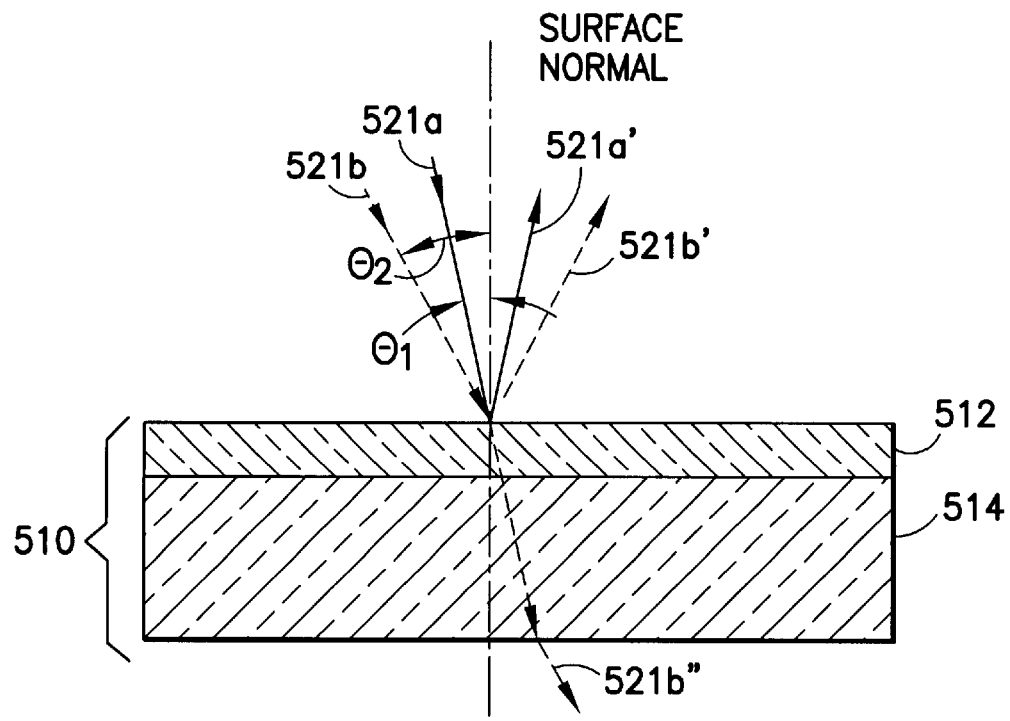
FIG. 4 is a schematic cross-sectional view of an optically transparent sample comprising an optically transparent thin film and an optically transparent substrate.
Figure 5:
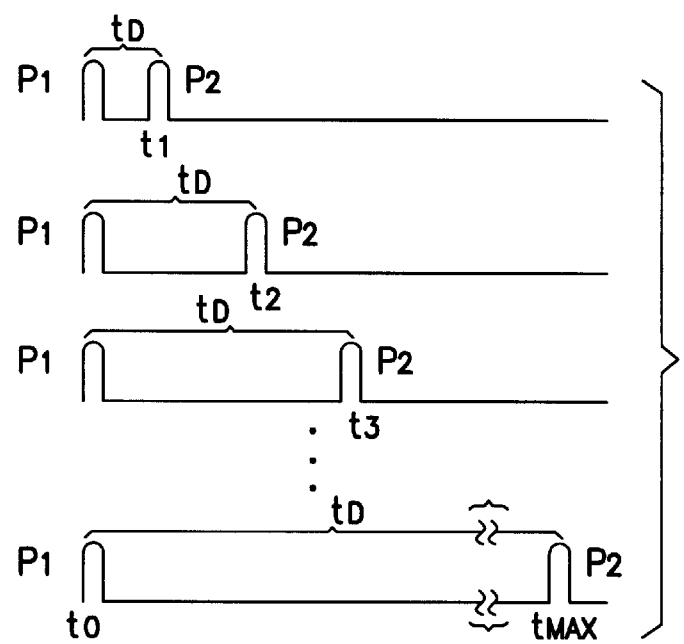
FIG. 5 illustrates a timed sequence of a plurality of consecutive pump pulses and corresponding probe pulses.

The sample stage 122 (see also FIG. 4) is preferably a multiple-degree of freedom stage that is adjustable in height (global z-axis), position (global x and y-axes), and optionally, tilt ($\phi$), and allows motor controlled positioning of a portion of the sample relative to the pump beam 1 and probe beam 2. The global z-axis is used to translate the sample vertically into the focus region of the pump beam 1 and probe beam 2, the global x and y-axes translate the sample parallel to the focal plane, and the tilt axes adjust the orientation of the stage 122 to establish a desired angle of incidence for the probe beam 2. This is achieved via position sensitive detector PSD1 and a signal processor 101, as described below.

In an alternative embodiment, the optical head may be moved relative to a stationary, tiltable stage 122' (not shown). This is particularly important for scanning large objects (such as 300 mm diameter wafers, or mechanical structures, etc.) In this embodiment the pump beam 1, probe beam 2, and video signal can be delivered to or from the translatable head via optical fibers or fiber bundles.

The pump-probe beam splitter 126 splits an incident laser beam pulse (preferably of picosecond or shorter duration) into pump beam(s) 1 and probe beam(s) 2, and includes a rotatable half-wave plate (WP1) that rotates the polarization of the unsplit beam. WP1 is used in combination with polarizing beam splitter PBS1 to effect a continuously variable split between pump and probe power. This split may be controlled by the computer by means of a motor to achieve an optimal signal to noise ratio for a particular sample. The appropriate split depends on factors such as the reflectivity and roughness of the sample. Adjustment is effected by having a motorized mount rotate WP1 under computer control.

A first acousto-optic modulator (AOM1) chops the pump beam 1 at a frequency of about 1 MHz. A second acousto-optic modulator (AOM2) chops the probe beam 2 at a frequency that differs by a small amount from that of the pump modulator AOM1. The use of AOM2 is optional in the system illustrated in FIG. 1A. Optionally, the AOMs may be synchronized to a common clock source, and may further be synchronized to the pulse repetition rate (PRR) of the laser that generates the pump beam 1 and probe beam 2. Optionally an electro-optic modulator can be used in place of acousto-optic modulators AOM1 or AOM2.

A spatial filter 128 is used to preserve at its output a substantially invariant probe beam profile, diameter, and propagation direction for an input probe beam which may vary due to the action of the mechanical delay line shown as a retroreflector 129. The spatial filter 128 includes a pair of apertures A1 and A 2, and a pair of lenses L4 and L5. An alternative embodiment of the spatial filter incorporates an optical fiber, as described above. If the profile of the probe beam 2 coming from the mechanical delay line does not vary appreciably as the retroreflector 129 is moved, the spatial filter 128 can be omitted.

WP2 is a second, adjustable, halfwave plate which functions in a similar manner with PBS2 to the WP1/PBS1 combination of the beam splitter 126. The part of the beam passing through the beam splitter PBS1 impinges on a beam block. Beam splitter BS2 is used to direct a small fraction of the probe beam 2 onto reference detector D2. The output of D2 is amplified and sent through a low pass filter to give an electrical signal LF2 which is proportional to the average intensity of the incident probe beam 2.

The probe beam 2, after passing through BS2, is focused onto the sample by lens L2. After reflection from the sample, the beam is collimated and after passing polarizer 132, the beam is incident on photodetector D1. From the output of D1 two electrical signals are derived. The first signal LF1 is obtained by passing the amplified output of D1 through a low pass filter to give an electrical signal proportional to the average intensity of the incident probe beam 2. The second signal HF1 is obtained by passing the amplified output of D1 through a high pass filter which passes the frequency of modulation used for AOM1.

The low frequency signals LF1 and LF2 can be used to determine the reflectivity of the sample, after allowance is made for fixed losses in both optical paths. The signal LF2 and the average (dc) output of detector D4 give a measure of the intensity of the pump beam 1 and probe beam 2. These signals are fed to a computer, for example the signal processor 101, which in turn controls motorized waveplates WP1 and WP2. The computer is programmed to adjust these waveplates so as to give the desired total optical power and pump/probe ratio for a sample exhibiting a particular reflectivity.

The linear polarizer 132 is employed to block scattered pump beam 1 polarization, and to pass the probe beam 2. The beamsplitter BS1 is used to direct a small part of the pump beam 1, and optionally a small part of the probe beam 2, onto a first Position Sensitive Detector (PSD1) that is used for autofocusing, in conjunction with the processor 101 and movements of the sample stage 122. The PSD1 is employed in combination with the processor 101 and the computer-controlled stage 122 (tilt and z-axis) to automatically focus the pump beam 1 and probe beam 2 onto the sample to achieve a desired focusing condition.

The detector D1 may be used in common for reflectometry, ellipsometry, and transient optical embodiments of this invention. However, the resultant signal processing is different for each application. For transient optical measurements, the DC component of the signal is suppressed, such as by subtracting reference beam input D2, or part of it as needed, to cancel the unmodulated part of D1, or by electrically filtering the output of D1 so as to suppress frequencies other than that of the modulation. The small modulated part of the signal is then amplified and stored. For ellipsometry, there is no small modulated part, rather the entire signal is sampled many times during each rotation of the rotating compensator (see discussion of FIG. 1B below), and the resulting waveform is analyzed to yield the ellipsometric parameters. For reflectometry, the change in the intensity of the entire unmodulated probe beam 2 due to the sample is determined by using the D1 and D2 output signals (D2 measures a signal proportional to the intensity of the incident probe). Similarly, additional reflectometry data can be obtained from the pump beam 1 using detectors D3 and D4. The analysis of the reflectometry data from either or both beams may be used to characterize the sample. The use of two beams is useful for improving resolution, and for resolving any ambiguities in the solution of the relevant equations.

A third beamsplitter BS3 is used to direct a small fraction of the pump beam 1 onto detector D4, which measures a signal proportional to the incident pump beam 1 intensity. A fourth beamsplitter BS4 is positioned so as to direct a small fraction of the pump beam 1 onto detector D3, which measures a signal proportional to the reflected pump beam intensity.

Figure 1B:
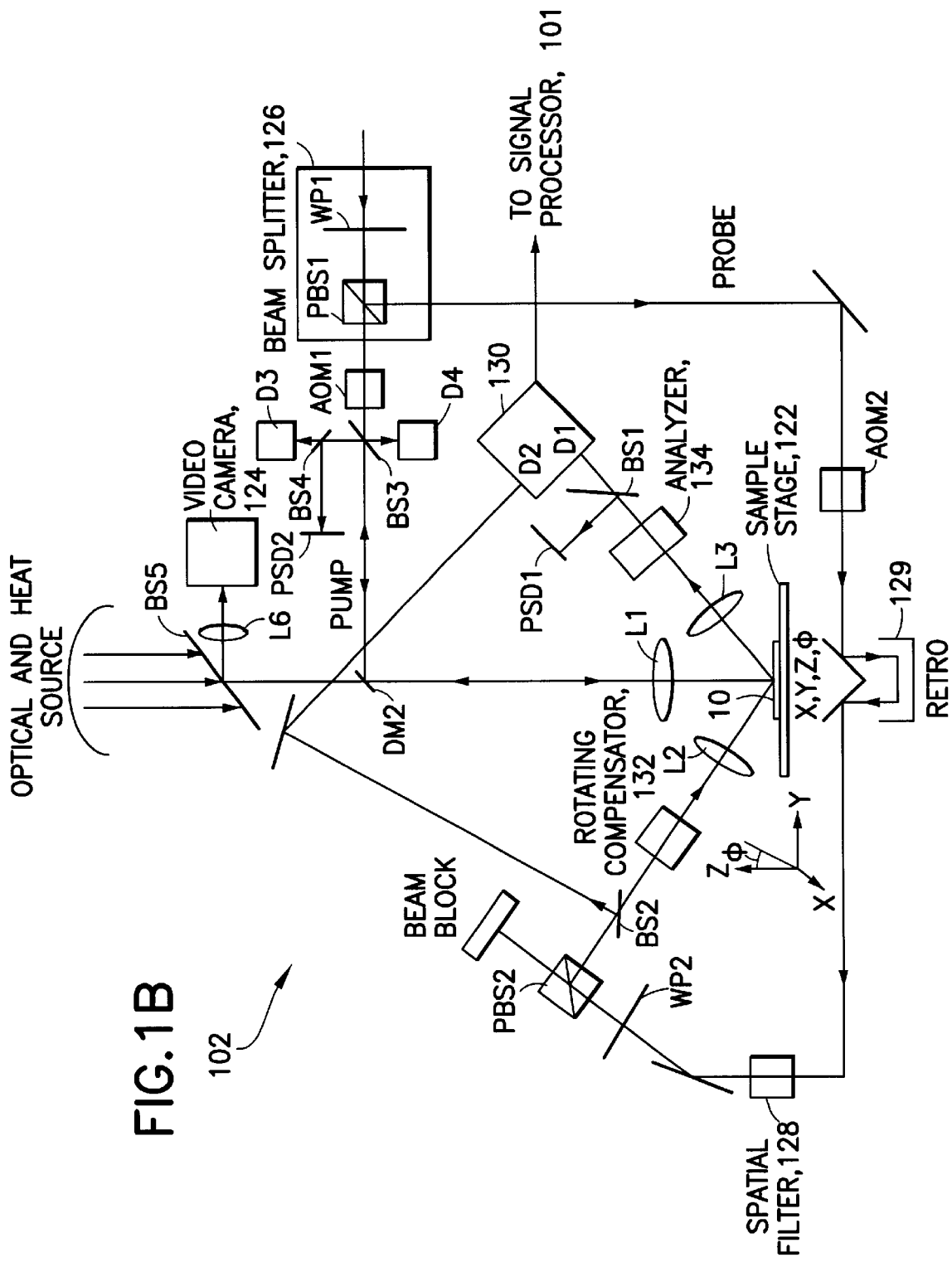
FIG. 1B is a block diagram of a second embodiment of an ultra-fast optical system that is suitable for use in practicing this invention, specifically, a normal pump, oblique probe embodiment.

FIG. 1B illustrates a normal pump beam, oblique probe beam embodiment of apparatus 102. Components labeled as in FIG. 1A function in a similar manner, unless indicated differently below. In FIG. 1B there is provided the above-mentioned rotating compensator 132, embodied as a linear quarter wave plate on a motorized rotational mount, and which forms a portion of an ellipsometer mode of the system. The plate is rotated in the probe beam 2 at a rate of, by example, a few tens of Hz to continuously vary the optical phase of the probe beam 2 incident on the sample. The reflected light passes through an analyzer 134 and the intensity is measured and transferred to the processor 101 many times during each rotation. The signals are analyzed according to known types of ellipsometry methods to determine the characteristics of the sample (transparent or semi-transparent films). This allows the (pulsed) probe beam 2 to be used to carry out ellipsometry measurements.

The ellipsometry measurements are carried out using a pulsed laser, which is disadvantageous under normal conditions, since the bandwidth of the pulsed laser is much greater than that of a CW laser of a type normally employed for ellipsometry measurements.

The ellipsometry measurement capability is useful in performing certain of the embodiments of the method described below, wherein it is required to determine the index of refraction of a film layer disposed over a substrate. Also, the ellipsometry measurement capability is useful wherein it may be advantageous to be able to determine the index of refraction of one or more film layers in a sample composed of several films.

If transient optical measurements are being made, the rotating compensator 132 is oriented such that the probe beam 2 is linearly polarized orthogonal to the pump beam 1. The analyzer 134 may be embodied as a fixed polarizer, and also forms a portion of the ellipsometer mode of the system. When the system is used for transient optical measurements the polarizer 134 is oriented to block the pump beam 1.

The analyzer 134 may be embodied as a fixed polarizer, and also forms a portion of the ellipsometer mode of the system. When used in the ellipsometer mode, the polarizer 134 is oriented so as to block light polarized at 45 degrees relative to the plane of the incident and reflected probe beam.

The embodiment of FIG. 1B further includes a dichroic mirror (DM2), which is highly reflective for light in a narrow band near the pump beam wavelength, and is substantially transparent for other wavelengths.

It should be noted in FIG. 1B that BS4 is moved to sample the pump beam 1 in conjunction with BS3, and to direct a portion of the pump beam 1 to D3 and to a second PSD (PSD2). PSD2 (pump PSD) is employed in combination with the processor 101, computer controlled stage 122 (tilt and z-axis), and PSD1 (Probe PSD) to automatically focus the pump beam 1 and probe beam 2 onto the sample to achieve a desired focusing condition. Also, a lens L1 is employed as a pump beam, video, and optical heating focussing objective, while an optional lens L6 is used to focus the sampled light from BS5 onto the video camera 124.

Figure 1C:
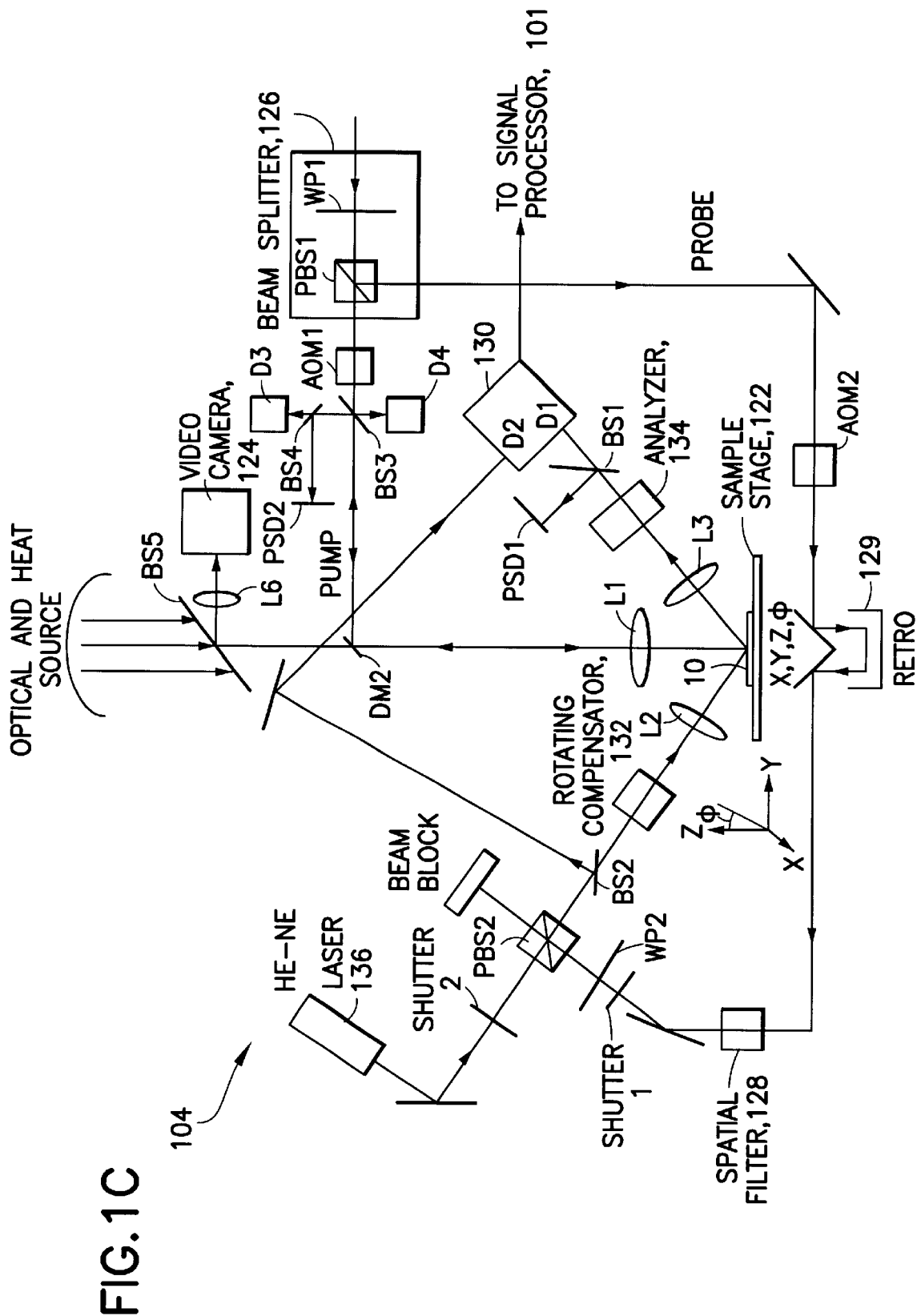
FIG. 1C is a block diagram of a third embodiment of an ultra-fast optical system that is suitable for use in practicing this invention, specifically, a single wavelength, normal pump, oblique probe, combined ellipsometer embodiment.

Reference is now made to FIG. 1C for illustrating an embodiment of apparatus 104, specifically a single wavelength, normal pump beam, oblique probe beam, combined ellipsometer embodiment. As before, only those elements not described previously will be described below.

Shutter 1 and shutter 2 are computer controlled shutters, and allow the system to use a He—Ne laser 136 in the ellipsometer mode, instead of the pulsed probe beam 2. For transient optical measurements shutter 1 is open and shutter 2 is closed. For ellipsometer measurements shutter 1 is closed and shutter 2 is opened. The HeNe laser 136 is a low power CW laser, and has been found to yield superior ellipsometer performance for some films.

Figure 1D:
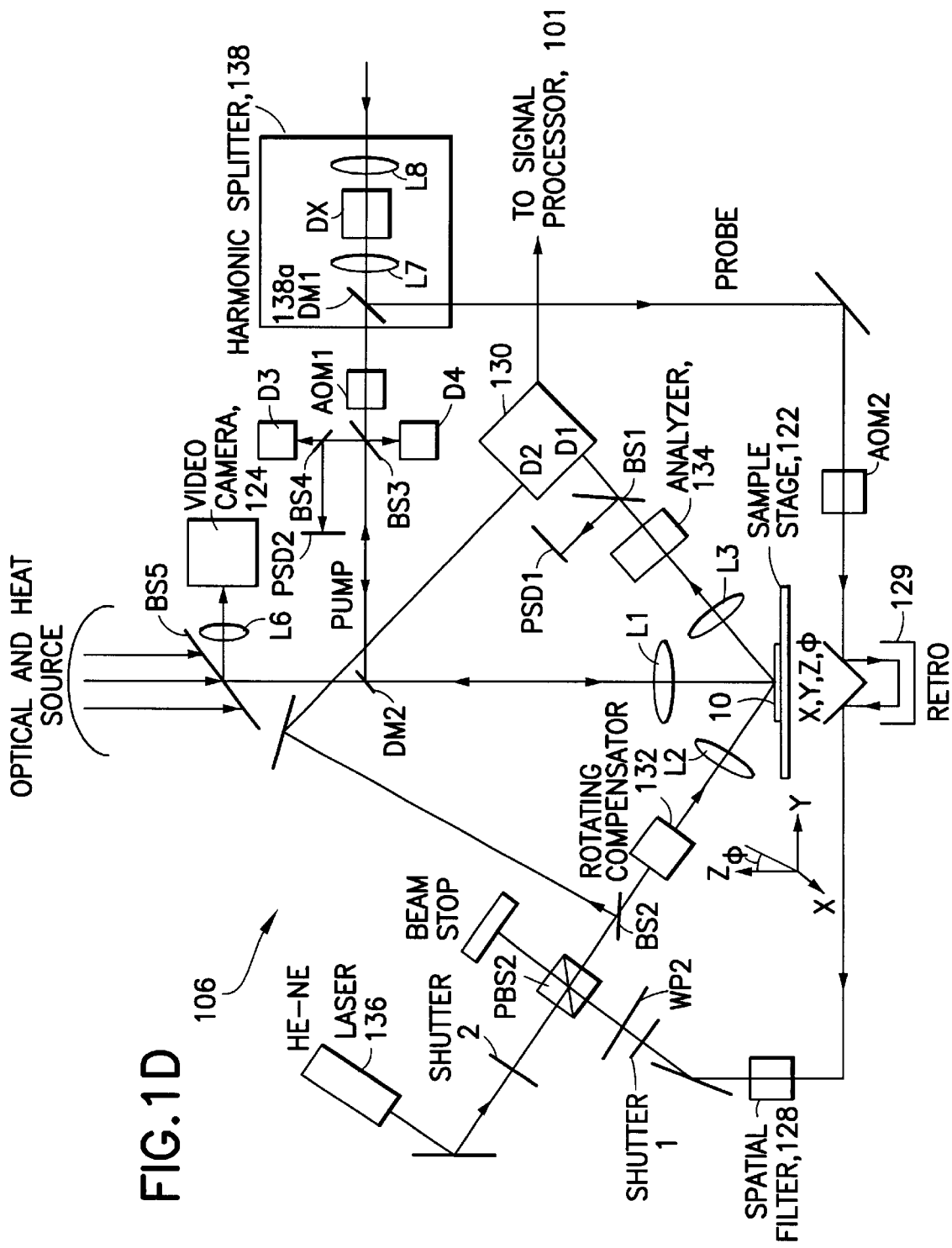
FIG. 1D is a block diagram of a fourth embodiment of an ultra-fast optical system that is suitable for use in practicing this invention, specifically, a dual wavelength, normal pump, oblique probe, combined ellipsometer embodiment.

FIG. 1D is a dual wavelength embodiment 106 of the system illustrated in FIG. 1C. In this embodiment the beamsplitter 126 is replaced by a harmonic splitter, an optical harmonic generator that generates one or more optical harmonics of the incident unsplit incident laser beam. This is accomplished by means of lenses L7, L8 and a nonlinear optical material (DX) that is suitable for generating the second harmonic from the incident laser beam. The pump beam 1 is shown transmitted by the dichroic mirror (DM1 138a) to the AOM1, while the probe beam 2 is reflected to the retroreflector. The reverse situation is also possible.

The shorter wavelength may be transmitted, and the longer wavelength may be reflected, or vice versa. In the simplest case the pump beam 1 is the second harmonic of the probe beam 2 (i.e., the pump beam 1 has one half the wavelength of the probe beam 2).

It should be noted that in this embodiment the AOM2 can be eliminated and instead a color filter F1 can be used in front of the detector D1 in order to reduce the amount of light reaching the detector D1. F1 is a filter having high transmission for the probe beam 2 and the He—Ne wavelengths, but very low transmission for the pump beam wavelength.

Figure 1E:
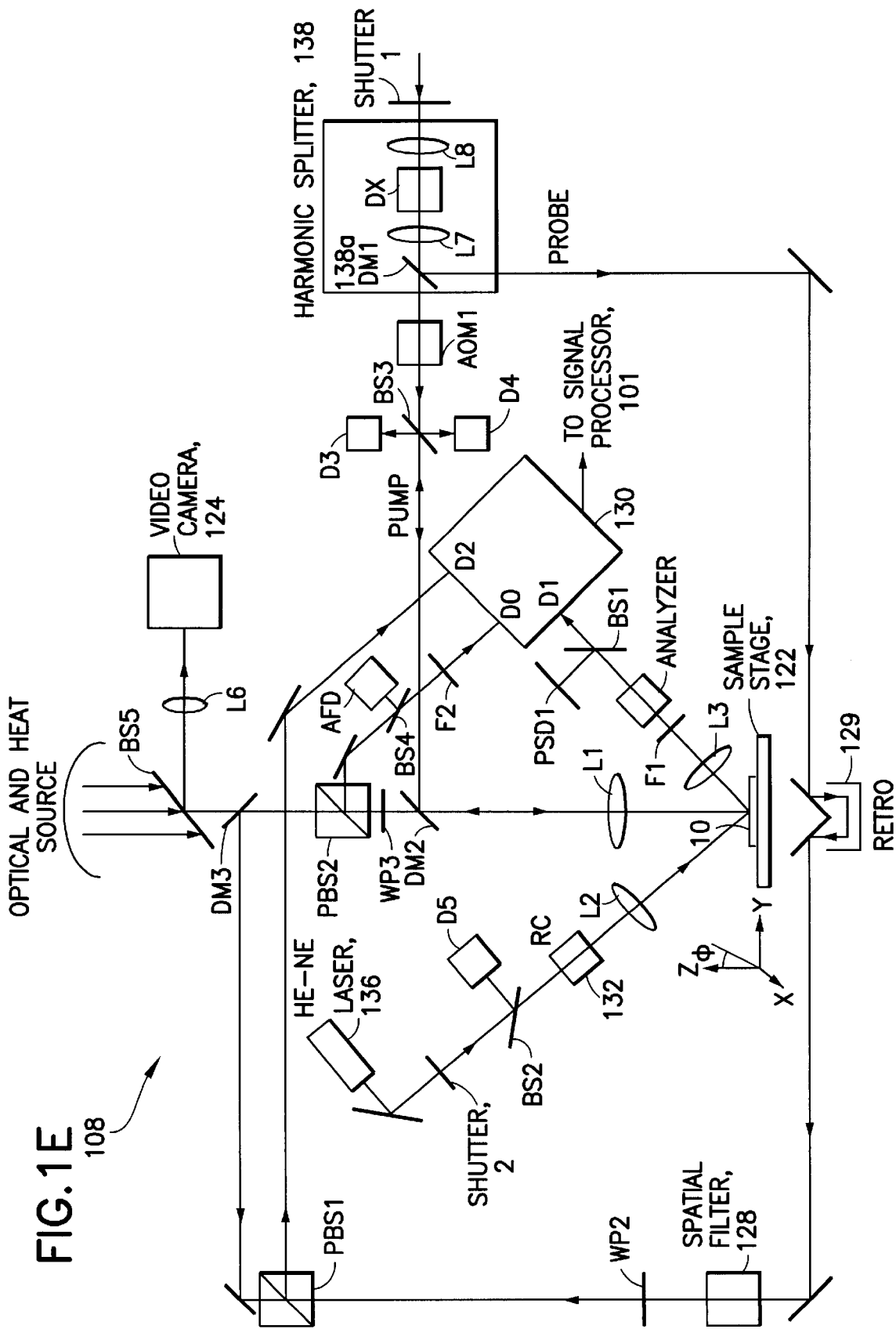
FIG. 1E is a block diagram of a fifth embodiment of an ultra-fast optical system that is suitable for use in practicing this invention, specifically, a dual wavelength, normal incidence pump and probe, combined ellipsometer embodiment.

Finally, FIG. 1E illustrates a normal incidence, dual wavelength, combined ellipsometer embodiment 108. In FIG. 1E the probe beam 2 impinges on PBS2 and is polarized along the direction which is passed by the PBS2. After the probe beam 2 passes through WP3, a quarter wave plate, and reflects from the sample, it returns to PBS2 polarized along the direction which is highly reflected, and is then directed to a detector D0 in detector block 130. D0 measures the reflected probe beam intensity.

In greater detail, WP3 causes the incoming plane polarized probe beam 2 to become circularly polarized. The handedness of the polarization is reversed on reflection from the sample, and on emerging from WP3 after reflection, the probe beam 2 is linearly polarized orthogonal to its original polarization. BS4 reflects a small fraction of the reflected probe onto an Autofocus Detector AFD.

DM3, a dichroic mirror, combines the probe beam 2 onto a common axis with the illuminator and the pump beam 1. DM3 is highly reflective for the probe wavelength, and is substantially transparent at most other wavelengths.

D1, a reflected He—Ne laser 136 detector, is used only for ellipsometric measurements.

It should be noted that, when contrasting FIG. 1E to FIGS. 1C and 1D, that the shutter 1 is relocated so as to intercept the incident laser beam prior to the harmonic splitter 138.

Based on the foregoing descriptions, a selected one of these presently preferred embodiments of measurement apparatus provide for the characterization of samples in which a short optical pulse (the pump beam 1) is directed to an area of the surface of the sample, and then a second light pulse (the probe beam 2) is directed to the same or an adjacent area at a later time. The retroreflector 129 shown in all of the illustrated embodiments of FIGS. 1A–1E can be employed to provide a desired temporal separation of the pump beam 1 and probe beam 2. FIG. 9 illustrates various time delays ($t_D$) between the application of a pump beam pulse (P1) and a subsequent application of a probe beam pulse (P2), for times ranging from $t_1$ to $t_{MAX}$.

The five embodiments 100, 102, 104, 106 and 108, as described above, have in common the feature that a sequence of pump beam pulses are generated and directed at the surface of the sample. Each pump beam pulse illuminates the same area of the sample with an intensity that varies smoothly across the area. The embodiments just described measure the change $\Delta R(t)$ in the optical reflectivity that results from the application of the pump light pulse. It is also within the scope of this invention to measure an alternate transient optical response. That optical response may be at least one electromagnetic characteristic of the probe beam 2 reflected from the sample, and the electromagnetic characteristic may include a modulated change in intensity of the probe beam 2 reflected from the sample, a change in a polarization of the probe beam 2 reflected from the sample, a change in an optical phase of the probe beam 2 reflected from the sample or a change in an angle of reflection of the probe beam 2 reflected from the sample. The modifications of the apparatus that are required in order for measurements of these different listed optical responses will be evident to those skilled in the art. For example, a change in the angle of reflection of the probe beam can be measured by means of a position sensitive detector. A change in the optical phase of the reflected probe beam can be measured by analyzing the reflected probe beam with an interferometer. In addition, multiple probe beams can be used and the relative phases of these beams, after reflection of at least one of the probe beams at the sample, can be determined by means of an interferometeric technique.

Figure 1F:
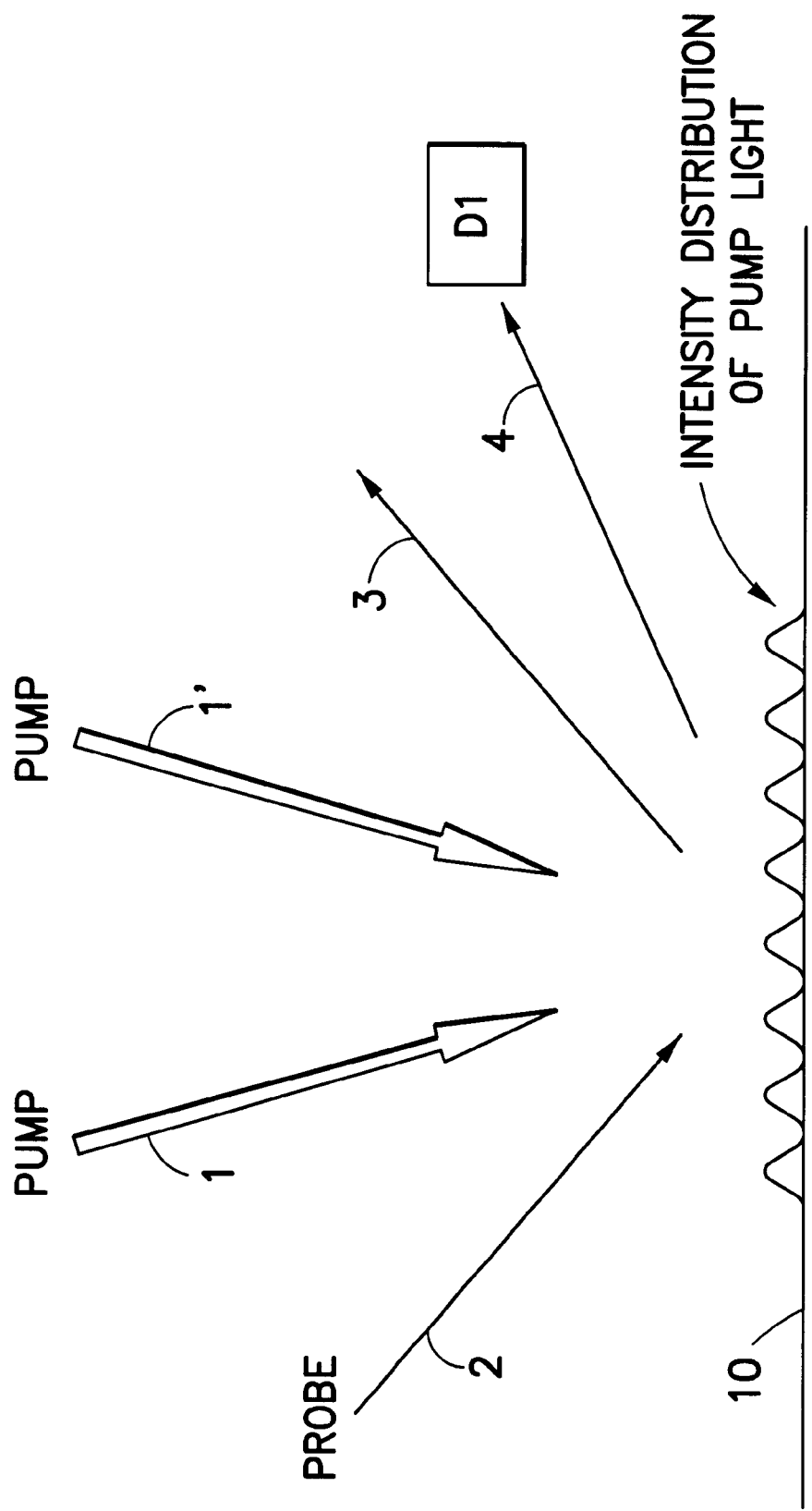
FIG. 1F illustrates the operation of a transient grating embodiment of this invention, wherein the pump pulse is divided and made to interfere constructively and destructively at the surface of the sample.

It is also within the scope of this invention to make measurements of the transient optical response by means of the induced transient grating method. (See: D. W. Phillion, D. J. Kuizenga, and A. E. Siegman, Appl. Phys. Lett. 27, 85 (1975)). To induce a transient grating each pump beam pulse is divided into two or more components by means of a beam splitter or beam splitters, these components then pass through separate optical paths, and are then all directed onto the same area of the surface of the sample 10. If the different components are directed onto the surface with different angles there will be places within the area where the different components interfere constructively and places where the interference is destructive. Thus the total intensity of the pump beam 1 will vary across the surface of sample 10. In the case that only two components 1 and 1' are present, as shown in FIG. 1F, the intensity will vary periodically across the surface, and consequently the transient changes in the optical properties of the sample 10 will also vary periodically across the surface of the sample 10. This variation of the transient changes in the optical properties of the sample 10 is equivalent to the production of a transient diffraction grating coinciding with the surface of sample 10. When probe beam 2 is incident on the area excited by the pump beam 1, a part 4 of the probe beam 2 be diffracted, i.e. a part of the probe beam 2 will be reflected in a direction, or directions, away from the direction 3 of specular reflection. Measurement of the intensity of this diffracted probe beam by means of the detector D1 as a function of the time delay t between the application of the pump beam 1 and probe beam 2 provides an alternate method for the characterization of the transient optical response produced in the sample 10.

Figure 2:
FIG. 2 illustrates a pulse train of pump beam pulses having an overlying low frequency intensity modulation impressed thereon.

Typical characteristics of the light pulses employed in the systems 100–108 of FIGS. 1A–1E are as follows. The pump pulse has an energy of approximately 0.001 to 100 Nj per pulse, a duration of approximately 0.01 psecs to 100 psec per pulse, and a wavelength in the range 200 nm to 4000 nm. The pulse repetition rate (PRR) is in the range of 100 Hz to 5 Ghz and, as is shown in FIG. 2, the pump pulse train may be intensity modulated at a rate of 1 Hz to 100 Mhz, depending on the PRR. The pump pulse is focussed to form a spot on the surface of sample 10 of a diameter in the range of approximately 10 micrometers to 20 micrometers, although smaller spot sizes, and hence smaller lateral resolutions, can also be employed.

Figure 3A:
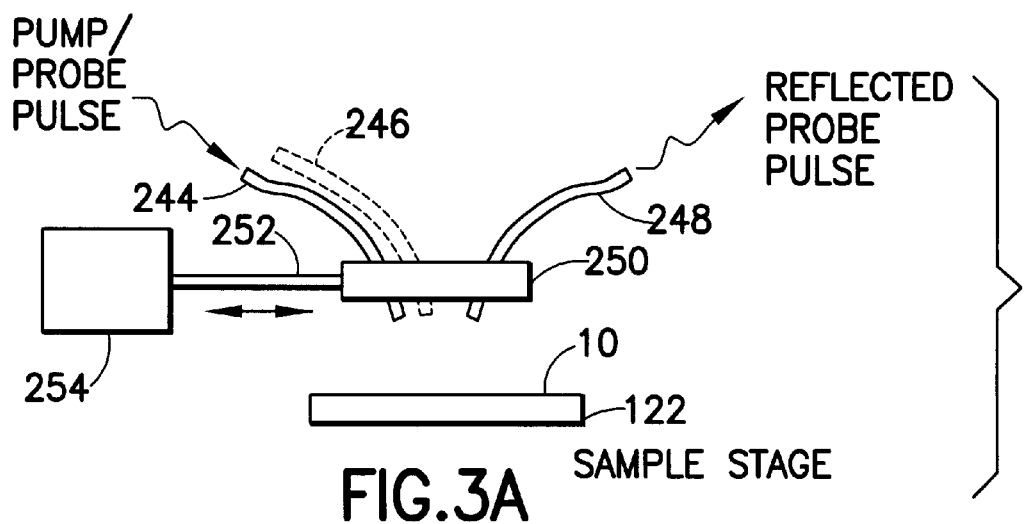
FIG. 3A illustrates a further embodiment wherein one or more optical fibers are positioned for delivering the pump beam and/or probe beam and for conveying away the reflected probe beam.

Referring to FIG. 3A, it is also within the scope of the teaching of this invention to deliver the pump beam 1, or the probe beam 2, or both, through an optical fiber 244. Alternatively, a second input fiber 246 can be provided, whereby the pump beam 1 is delivered through the fiber 244 and the probe beam 2 is delivered through the fiber 246. Another fiber 248 can also be employed for receiving the reflected probe beam and delivering same to the photodetector (not shown). For this embodiment the end of the optical fiber(s) are affixed to and supported by a holding stage 250. The holding stage 250 is preferably coupled through a member 252 to an actuator 254, such as a linear actuator or a two degree of freedom positioning mechanism. In this manner the reliability and repeatability of the measurement cycle is improved, in that the size and position of the focussed pump beam 1, probe beam 2, or both, on the surface of sample 10 are independent of minor changes in the direction or profile of the laser output beams, or changes in the profile of the probe beam 2 associated with the motion of any mechanical stage that may be used to effect the delay $t_D$. Preferably, the angular orientation between the end of the probe beam delivery fiber and the end of the reflected probe beam fiber is such as to optimize the gathering of reflected probe beam light from the surface of sample 10. It is also within the scope of this invention to use one or more lenses following the fiber or fibers, in order to focus the output beams from the fibers onto the surface of sample 10, or to collect the reflected probe beam 2 and to direct it into the fiber 248 of FIG. 3A.

Figure 3B:
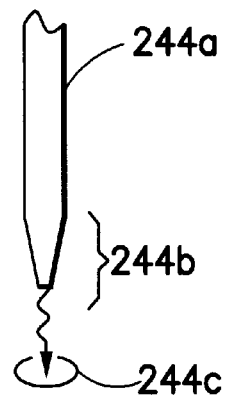
FIG. 3B illustrates a terminal end of a fiber optic that has been reduced in cross-sectional area for delivering an optical pulse to a small surface area of a sample.

FIG. 3B shows an embodiment wherein a terminal portion 244b of a pump and/or probe beam delivery fiber 244a is reduced in diameter, such as by stretching the fiber, so as to provide a focussed spot 244c having a diameter that is less than the normal range of optical focussing. When coupled with the embodiment of FIG. 3A this enables the pump and or probe optical pulse to be repeatably delivered to a very small region of the surface of sample 10 (e.g., to a spot having a diameter≦one micrometer), regardless of any changes that are occurring in the optical path length of the probe beam 2.

When the pump beam pulse is absorbed in the sample 10, the pulse energy is first transferred to the conduction electrons in the metal film. Electrons are excited from occupied states below the Fermi energy to empty states above the Fermi level. This change in the distribution of electrons amongst the states results in a change $\Delta R_{electron}(t)$ in the optical reflectivity of the sample 10. The probability that an electron will make a transition from an initial state to a particular final state is determined by a transition matrix element which involves the wave functions of the electron in the two states and the spatial variation of the oscillating electromagnetic field inside the sample 10 due to the application of the pump beam 1. The transition probability depends on the crystallographic orientation of the surface of the sample 10. In addition, for a given change in the distribution of the electrons, the transient change in optical reflectivity $\Delta R_{electron}(t)$ depends on the crystallographic orientation of the surface of the sample 10.

After the electrons have been excited, they diffuse away from the surface into the interior of the metal film. The electrons lose energy by emission of thermal phonons and the temperature of the film is increased. This increase in temperature of the film results in a thermal stress distribution with the film. The stress distribution causes a strain pulse to be generated, and this strain pulse bounces back and forth inside the film. Each time that the strain pulse returns to the top surface of the film, it results in a small change in the optical properties of the film near to the surface. This change, in turn, causes a transient change in optical reflectivity $\Delta R_{strain}(t)$. If the sample 10 is a single metallic film deposited on a substrate, this change is characterized by a series of sharp features ("echoes") with an interval between them equal to the time for a strain pulse to make one round trip in the sample 10. As just mentioned, the change $\Delta R_{strain}(t)$ in optical reflectivity arises because the strain pulse causes a change in the optical constants of the film material near to its upper surface. The magnitude of $\Delta R_{strain}(t)$, and also the shape of the echo, are determined by the piezo-optic tensor $\vec{W}$ of the material, by the direction of polarization of the probe beam 2, by the angle of incidence of the probe beam 2, and by the crystallographic orientation of the surface.

As a highly simplified example, assume that the strain pulse produces a uniform strain $\vec{\eta}$ in the region of the metal film close to the surface, and assume further that the probe beam pulse is at normal incidence. The change in optical reflectivity (M. Cardona, Modulation Spectroscopy, Academic Press, 1969, chapter 20) is then given by the formula $$\frac{\Delta R_{strain}}{R} = \hat{n} \cdot (\vec{Q} \cdot \vec{\eta}) \cdot \hat{n} \qquad (1)$$

where $\hat{n}$ is the normal to surface, and $\vec{Q}$ is the piezo-reflectance tensor which can readily be related to the piezo-optic tensor $\vec{W}$ (see M. Cardona, Modulation Spectroscopy, Academic Press, 1969, chapter 8). The piezo-optic and piezo-reflectance tensors are fourth rank tensors. For an amorphous material these tensors are isotropic, whereas for crystalline materials they are anisotropic. Thus, the magnitude and the shape of $\Delta R_{strain}(t)$ is dependent on the orientation of the crystal surface. For example, U. Gerhardt (Physical Review, 172, p. 651–664, 1968) has measured the components of $\vec{Q}$ for copper (a material of particular current interest in the semiconductor industry), for photon energies from about 1.5 to 5.5 eV (wavelength 8300 Å to 2260 Å). From these results, one may calculate the ratio of the magnitude of $\Delta R_{strain}$ for a longitudinal strain normal to the surface. The result is that $\Delta R_{strain}$ at a (111) surface is approximately six times larger than at a (100) surface. It is noted that the strain pulse that is generated by the pump pulse will not result in a strain pulse that gives a uniform strain near the surface. However, it is expected that regardless of the precise shape of the strain pulse, a significant dependence of the magnitude of $\Delta R_{strain}$ on the orientation of the crystal surface will be evident.

Another contribution to the total change in reflectivity comes from a change in temperature of the metal film. This results in a change in the optical constants of the film and leads to a thermoreflectance contribution $\Delta R_{thermal}$ to the total reflectivity change. The contribution $\Delta R_{thermal}$ also has a magnitude that depends on the crystallographic orientation of the surface of the film.

Thus, the total change $\Delta R(t)$ in optical reflectivity that is measured can be shown to be the sum of three contributions, i.e.

$$\Delta R(t) = \Delta R_{electron}(t) + \Delta R_{strain}(t) + \Delta R_{thermal}(t). \qquad (2)$$

Figure 7:
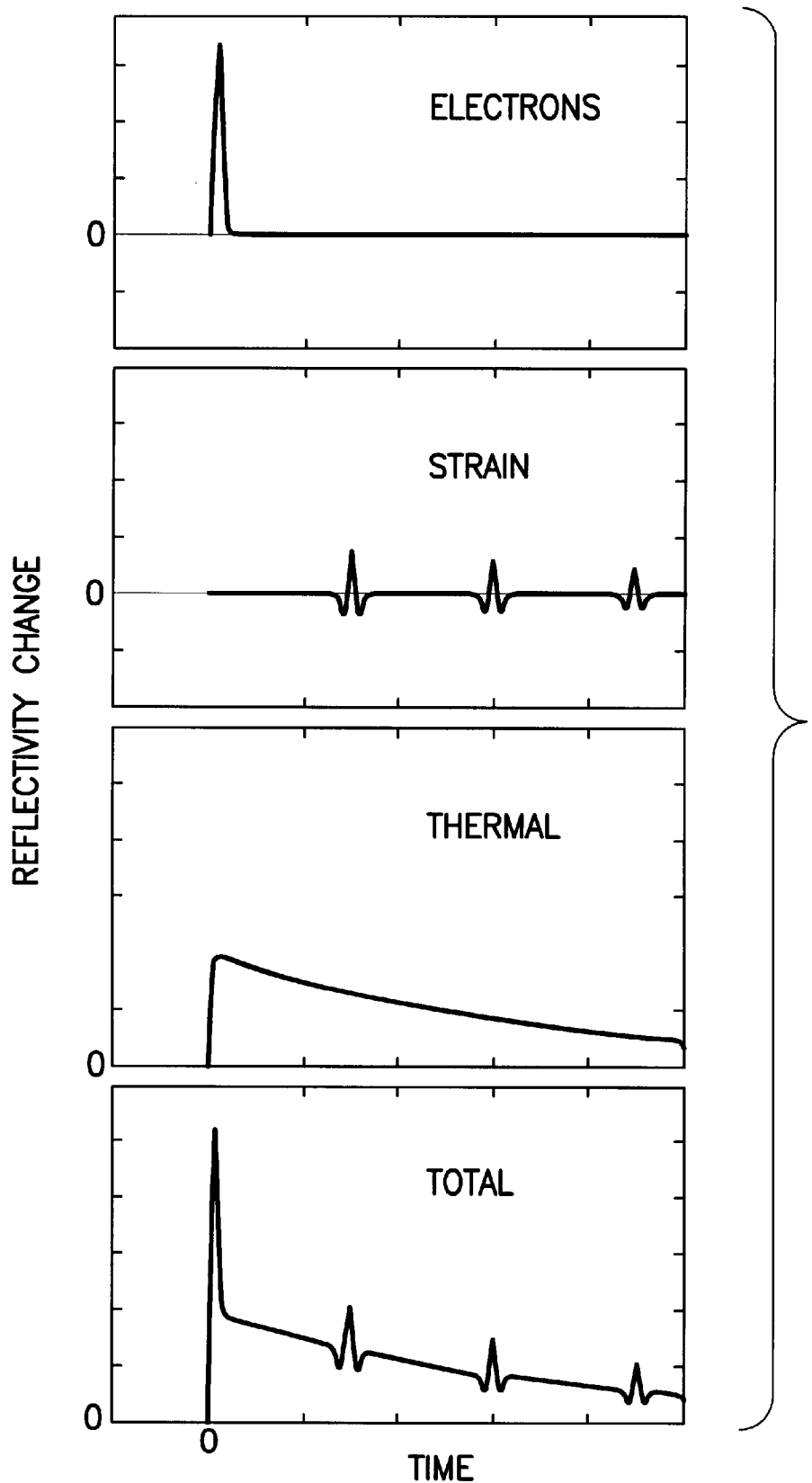

Because the three components, $\Delta R_{electron}$, $\Delta R_{strain}$, and $\Delta R_{thermal}$ vary in time in a very different manner, it is possible to determine the three components from the measurement of the single quantity $\Delta R(t)$. Specifically, 1) $\Delta R_{electron}$ is characterized by a sharp peak just after time zero, 2) $\Delta R_{strain}$ is characterized by a series of echoes, and 3) $\Delta R_{thermal}$ is characterized by a sharp jump at t=0 followed by a steady decay. These components are shown in FIG. 7.

As already described, each of these three components depends on the orientation of the crystal surface. Hence, in accordance with the teachings of this invention, a measurement of one or more of these components, or the ratio of two or more components, may be used to deduce the orientation of the film surface. The term orientation is used here to mean the average orientation of the grains that make up the crystal surface within the region that is illuminated by the pump beam 1 and the probe beam 2. The lateral dimensions D of the grains may be less than or greater than the linear dimensions ζ of the illuminated area. In the case that D>ζ, just one grain is measured and the orientation of this grain can be determined. If D<<ζ, the average orientation of a large number of grains will be measured.

Figure 6:
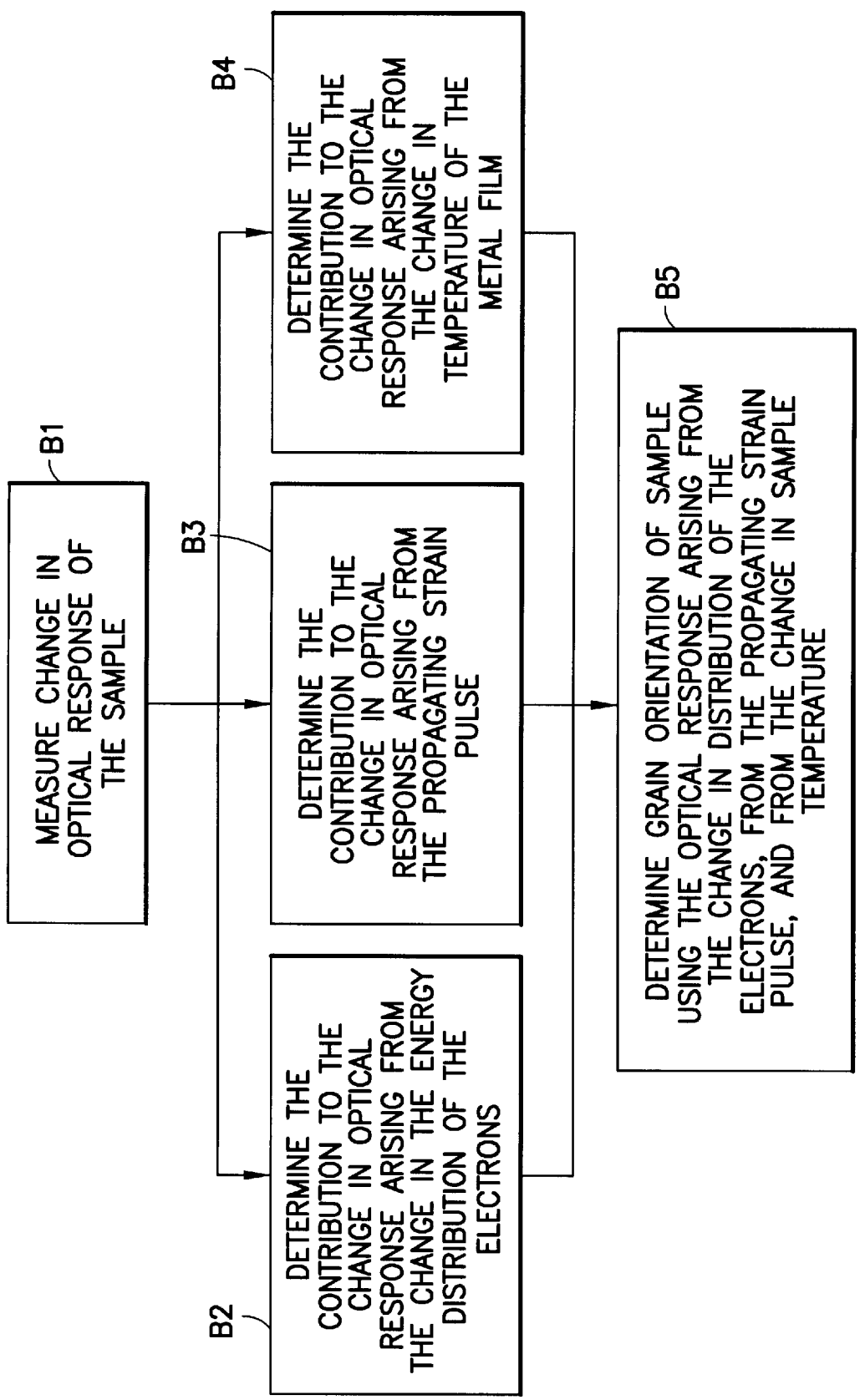
FIG. 6 is a flow chart depicting a presently preferred method for measuring the grain orientation in a sample; and, FIG. 7 shows a relationship over time between a total change $\Delta R$ (t) in optical reflectivity and three components of that change.

Examples of various methods that exploit the foregoing discovery are now provided.

a) Measurements can be made with an optical system in which all parameters, such as the energies of the pump and probe pulses, the area of the sample 10 onto which these are focussed, the sensitivity of the detectors, etc, are accurately controlled. As shown in FIG. 6, in block 1, a change in the optical response of the sample is measured. From blocks 2, 3, and 4, the components $\Delta R_{electron}(t)$, $\Delta R_{strain}(t)$, and $\Delta R_{thermal}(t)$ are determined. The components $\Delta R_{electron}(t)$, $\Delta R_{strain}(t)$, and $\Delta R_{thermal}(t)$ may be determined in parallel or serially. As shown in block 5, from these components, the grain orientation of the sample is determined.

b) Measurements can be made with an optical system as described above in a) and one or more of the components $\Delta R_{electron}(t)$, $\Delta R_{strain}(t)$, and $\Delta R_{thermal}(t)$ are determined, and compared with the magnitude of these components for a number of reference samples in which the grains have a known orientation. From this comparison, the average grain orientation in the unknown sample 10 is determined.

c) Measurements can be made with an optical system in which the parameters, such as the energies of the pump and probe pulses, the area of the sample 10 onto which these are focussed, the sensitivity of the detectors, etc, are not precisely known. Two or more of the components $\Delta R_{electron}(t)$, $\Delta R_{strain}(t)$, and $\Delta R_{thermal}(t)$ are determined, and the ratio of the magnitudes of these components are compared with the same ratio measured for reference samples in which the grains have a known orientation. From this comparison, the average grain orientation in the unknown sample 10 is determined.

The method can also be applied to measure the grain orientation in individual films making up a more complex structure composed of a number of thin films deposited onto a substrate. It can also be applied to laterally patterned structures.

The teachings of this invention include the use of the information obtained about the grain orientation to make possible more accurate measurements of the thickness of films. The thickness d of a film can be determined through a measurement of the time τ for a sound pulse to make a round trip in the film. The thickness is thus given by $$d = \frac{v\tau}{2}, \quad (3)$$

where v is the sound velocity. For some materials, the sound velocity varies by a significant amount according to the direction in which the sound propagates in the crystal. For copper, for example, the sound velocity in the (100), (110), and (111) crystal orientation directions is 43, 50 and 52 Å / psec, respectively. Thus, if the average crystallographic orientation of the grains in the film is unknown, the uncertainty in the sound velocity results in a significant uncertainty in the estimated thickness. To overcome this difficulty the following procedure can be used.

1) The average grain orientation is first determined by one of the methods already described.
2) The sound velocity for this orientation is calculated. This can be accomplished, for example, by a) taking a suitable weighted average of the velocities in the (100), (110), and (111) crystal orientation directions, or by (b) using measured data for the sound velocity obtained from a sample of known thickness and the same average grain orientation as determined in 1). Other methods can also be used.
3) The thickness of the film is then found from Eq. 3.

The various methods described above can be implemented using the processor 101 shown in FIGS. 1A–1E, either in whole or in cooperation with an external data processor.

It is important to note that in a further embodiment, blocks 1 through 5 of FIG. 6 may implemented in hardware to accomplish the functions described in each respective block.

The teachings of this invention include the use of the information obtained about the grain orientation to determine whether a film has been annealed or has been annealed correctly. When a film has been annealed, its average grain orientation may change in a characteristic way. A measurement of the grain orientation then, may confirm that an annealing step has taken place, or that an annealing step has been completed, i.e. that the annealing was done according to a predetermined set of conditions. By example, an annealing process may include a particular temperature profile where the temperature of the film is raised at a predetermined rate, held at a specified temperature for a period of time and then lowered at a predetermined rate. After annealing according to the particular temperature profile, the sample preferably has a particular grain orientation characteristic. As stated above, the grain orientation measurements may be made with an optical system in which all parameters are accurately controlled and the grain orientation measured directly. Alternatively, measurements can be made with an optical system as described above where one or more of the components $\Delta R_{electron}(t)$, $\Delta R_{strain}(t)$, and $\Delta R_{thermal}(t)$ are determined, and compared with the magnitude of these components for a number of reference samples. Further, measurements may be made with an optical system in which the parameters are not precisely known, and two or more of the components $\Delta R_{electron}(t)$, $\Delta R_{strain}(t)$, and $\Delta R_{thermal}(t)$ are determined, and the ratio of the magnitudes of these components are compared with the same ratio measured for reference samples in which the grains have a known orientation. In the case where reference samples are used for comparison, both the samples and the reference samples have preferably been deposited on substrates under similar conditions.

While the invention has been particularly shown and described with respect to preferred embodiments thereof, it will be understood by those skilled in the art that changes in form and details may be made therein without departing from the invention. Accordingly, the present invention is intended to embrace all such alternatives, modifications and variances which fall within the scope of the appended claims.

What is claimed is:

1. A method for determining grain orientation in a sample, the method comprising the steps of:
    measuring a first transient optical response of the sample;
    determining the contribution to the transient optical response arising from a change in the energy distribution of the electrons in the sample;
    determining the contribution to the transient optical response arising from a propagating strain pulse within the sample;
    determining the contribution to the transient optical response arising from a change in sample temperature; and
    determining the grain orientation of the sample using said contributions to the transient optical response arising from the change in the energy distribution of the electrons, the propagating strain pulse, and the change in sample temperature.

2. A method as in claim 1, wherein the step of measuring a first transient optical response comprises measuring the first transient optical response of the sample as a function of time.

3. A method as in claim 1, wherein the step of measuring a first transient optical response comprises measuring an amplitude of the first transient optical response.

4. A method as in claim 1, wherein the step of measuring a first transient optical response comprises measuring at least one electromagnetic characteristic of a probe beam reflected from the sample, the electromagnetic characteristic being a modulated change in intensity of the probe beam reflected from the sample, a change in a polarization of the probe beam reflected from the sample, a change in an optical phase of the probe beam reflected from the sample or a change in an angle of reflection of the probe beam reflected from the sample.

5. A method as in claim 1, wherein the step of measuring a first transient optical response comprises measuring a change in an optical phase of one or more probe beams reflected from the sample using an interferometeric technique.

6. A method as in claim 1, wherein said contributions to the transient optical response arising from the change in the energy distribution of the electrons, the propagating strain pulse, and the change in sample temperature have different time dependent characteristics.

7. A method as in claim 1 wherein the sample is a thin film having a thickness of between about 30 A and about 10μ, the thin film being disposed on a substrate.

8. A method as in claim 1, wherein the sample is comprised of a metal film wherein said metal is one of the group of aluminum, cobalt, copper, nickel, titanium, or tungsten.

9. A method as in claim 1, wherein the sample is comprised of a film of one of polysilicon or titanium nitride.

10. A method as in claim 1, wherein the sample includes a stack comprising a plurality of thin films and wherein the step of determining the grain orientation of the sample comprises using said contributions to the transient optical response arising from the change in the energy distribution of the electrons, the propagating strain pulse, and the change in sample temperature of a predetermined film in the stack to determine the grain orientation of said predetermined film in the stack.

11. A method as in claim 1, wherein the step of determining the grain orientation further comprises:

comparing a characteristic of said sample, said characteristic comprising contributions to the transient optical response arising from at least one of the change in the energy distribution of the electrons, the propagating strain pulse, and the change in sample temperature of said sample, to a corresponding characteristic of at least one reference sample having a known grain orientation; and, determining the grain orientation of the sample from the grain orientation of said at least one reference sample.

12. A method as in claim 1, wherein the step of determining the grain orientation comprises:

determining a ratio of the magnitudes of at least two characteristics, said characteristics comprising said contributions to the transient optical response arising from the change in the energy distribution of the electrons, the propagating strain pulse, and the change in sample temperature of the sample; and, determining the grain orientation of the sample from the grain orientation of at least one reference sample selected by comparing said ratio of at least two characteristics with a ratio of said at least two characteristics of at least one reference sample having a known grain orientation.

13. A method as in claim 1, wherein the step of measuring the first transient optical response comprises the steps of:

applying a first pulse of light to a surface of the sample for creating a propagating strain pulse in the sample;

applying a second pulse of light to the surface of the sample, the second pulse of light being temporally delayed relative to the first pulse of light so that the second pulse of light interacts with the propagating strain pulse in the sample; and sensing from a reflection of the second pulse of light from the sample the first transient optical response of the sample.

14. A method as in claim 1, wherein the step of measuring the first transient optical response comprises the steps of:

applying a plurality of pump light pulses to the sample to result in constructive and destructive interference therebetween and induce a spatially varying strain pulse in the sample;

applying a probe beam pulse to interact with the strain pulse in the sample; and detecting from a diffracted portion of the probe beam pulse the first transient optical response of the sample.

15. A method as in claim 1 further comprising the steps of:

determining the velocity of sound through the sample;

determining the propagation time of a strain pulse through the sample; and, determining thickness of the sample from said grain orientation of the sample, said velocity of sound through the sample, and said propagation time of a strain pulse through the sample.

16. A method as in claim 1 further comprising the step of comparing said grain orientation of the sample with the grain orientation of a reference sample that has been annealed according to a predefined set of conditions in order to determine that the sample has been annealed according to the same set of predefined conditions, said sample and reference sample having been deposited on a substrate under similar conditions.

17. A method according to claim 16 wherein said set of predetermined conditions comprises a predetermined temperature profile.

18. A method for determining the thickness of a sample comprising the steps of:

determining the grain orientation of the sample from a detected transient optical response of a sample to a pump pulse, as indicated by a temporally delayed probe pulse;

determining the velocity of sound through the sample in accordance with the determined grain orientation of the sample;

determining the propagation time of a strain pulse through the sample; and, determining the thickness of the sample from said grain orientation of the sample, said velocity of sound through the sample, and said propagation time of a strain pulse through the sample.

* * * * *